United States Patent
Daugs et al.

(10) Patent No.: US 8,722,944 B2
(45) Date of Patent: May 13, 2014

(54) PROCESS FOR OLEFIN ETHERIFICATION

(75) Inventors: Edward D. Daugs, Midland, MI (US);
Derrick W. Flick, Midland, MI (US);
Cynthia L. Rand, Sanford, MI (US);
Michael L. Tulchinsky, Midland, MI (US); Wanglin Yu, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 807 days.

(21) Appl. No.: 12/430,171

(22) Filed: Apr. 27, 2009

(65) Prior Publication Data

US 2009/0281359 A1 Nov. 12, 2009

Related U.S. Application Data

(60) Provisional application No. 61/051,900, filed on May 9, 2008.

(51) Int. Cl.
*C07C 41/06* (2006.01)
*C07C 43/12* (2006.01)

(52) U.S. Cl.
USPC ............................................. 568/697

(58) Field of Classification Search
None
See application file for complete search history.

(56) References Cited

U.S. PATENT DOCUMENTS

| | | | |
|---|---|---|---|
| 2,067,385 A | 1/1937 | Evans et al. | |
| 4,139,566 A | 2/1979 | Kim et al. | |
| 4,371,716 A | 2/1983 | Paxson et al. | |
| 4,906,787 A * | 3/1990 | Huang et al. | 568/697 |
| 5,026,459 A | 6/1991 | Quang et al. | |
| 5,030,768 A | 7/1991 | Chen et al. | |
| 5,258,560 A | 11/1993 | Marker | |
| 2004/0210093 A1* | 10/2004 | Groten et al. | 568/59 |

FOREIGN PATENT DOCUMENTS

| | | |
|---|---|---|
| DE | 2450667 | 4/1975 |
| EP | 0310194 A1 | 4/1989 |
| EP | 0747339 B1 | 12/1996 |
| EP | 0846671 A2 | 6/1998 |
| EP | 0850907 B1 | 7/1998 |
| JP | 2006282558 | 10/2006 |
| NL | 6607907 | 12/1967 |
| WO | 03104168 A2 | 12/2003 |

OTHER PUBLICATIONS

Bakker et al. (The Journal of the American Oil Chemist Society, vol. 44, Issue. 9, Sep. 1967, pp. 517-521).*
Bakker et al., "An Exploratory Study of the Addition Reactions of Ethyleneglycol, 2-Chloroethanol and 1,3-Dichloro-2-Propanol to 1-Dodecene", The Journal of the American Oil Chemists' Society, 1967, pp. 517-521, vol. 44.
Sundmacher et al., "Development of a new catalytic distillation process for fuel ethers via a detailed nonequilibrium model", Chemical Engineering Science, 1996, pp. 2359-2368, vol. 51 No. 10, Elsevier Science Ltd.

(Continued)

*Primary Examiner* — Rosalynd Keys

(57) ABSTRACT

The invention relates to processes for the etherification of olefins with alcohols. According to one aspect, a heterogeneous etherification catalyst is used under conditions that permit limiting the contact time between the desired product and the catalyst, thereby mitigation reverse reactions. According to a second aspect, a recycling process is used that significantly increases the yield of desired product.

13 Claims, 3 Drawing Sheets

(56) References Cited

OTHER PUBLICATIONS

Figure 1:
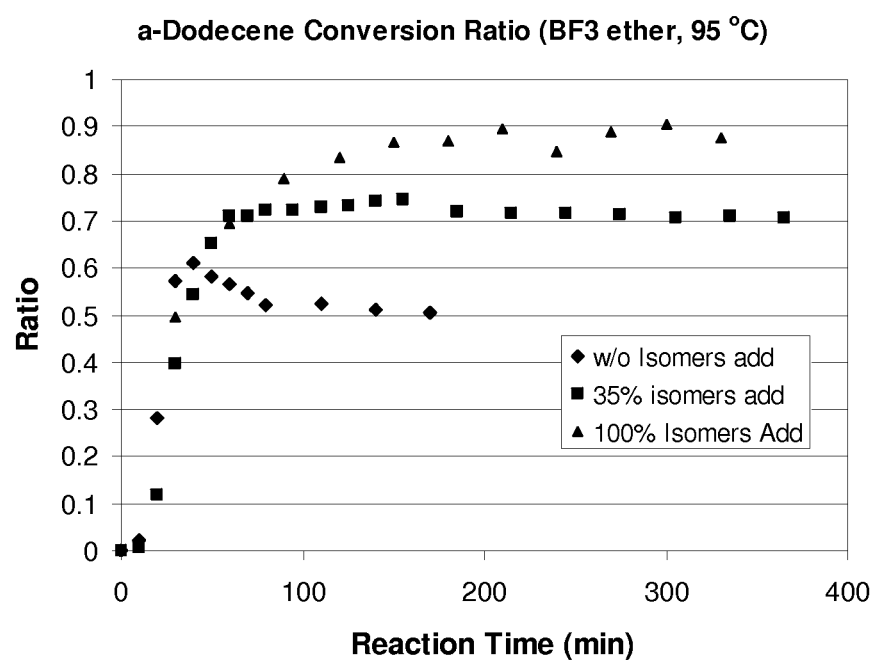

Bakker et al., Sulfonates and sulfates of sec-alkyl ethyl ether: dethergent prepared by the addition of substituted alcohols to 1-alkenes, Chim. Phys. Appl. Prat. Ag. Surface, 1968, 157-64, 1. Abstract provided.

Munro-Leighton et al., "Addition of N—H and O—H Bonds of Amines and Alcohols to Electron-Deficient Olefins Catalyzed by Monomeric Copper(I) Systems: Reaction Scope, Mechanistic Details, and Comparison of Catalyst Efficiency", Organometallics, 2007, pp. 1483-1493, vol. 26, American Chemical Society.

Matsukawa et al., "Palladium(0)-Catalyzed Hydroalkoxylation of Hexafluoropropene: Synthesis of Hydrofluoroethers under Neutral Conditions", Angew. Chem. Int. Ed, 2005, pp. 1128-1130, vol. 44, Wiley-VCH Verlag GmbH & Co. KGaA.

Murtagh et al.,"Novel amine-catalysed hydroalkoxylation reactions of activated alkenes and alkynes", Chem. Communication, 2005, pp. 227-229, The Royal Society of Chemistry.

Lemechko et al., "Hydroalkoxylation of non-activated olefins catalysed by Lewis superacids in alcoholic solvents: an eco-friendly reaction",Tetrahedron Letters, 2007, pp. 5731-5734, vol. 48, Elsevier Ltd.

Rosenfeld et al., "Hydroamination and Hydroalkoxylation Catalyzed by Triflic Acid. Parallels to Reactions Initiated with Metal Triflates", Organic Letters, 2006, pp. 4179-4182, vol. 8 No. 19., American Chemical Society.

Hensen et al., "Alkoxylation of limonene and alpha-pinene over beta zeolite as heterogeneous catalyst", Applied Catalysis A: General, 1997, pp. 311-329, vol. 149, Elsevier Science B.V.

OE et al., "Ruthenium-Catalyzed Addition Reaction of Alcohols across Olefins", Synlett, 2005, pp. 179-181, No. 1, Georg Thieme Verlag Stuttgart.

Gasanov et al., "Features of the Catalytic Addition of Monohydric and Dihydric Alcohols to Bicyclo[2.2.1]Heptenes", Russian Journal of Organic Chemistry, 1994, pp. 749-751, vol. 30 No. 5, Plenum Publishing Corporation.

\* cited by examiner

PROCESS FOR OLEFIN ETHERIFICATION

CROSS-REFERENCE TO PRIOR APPLICATION

This application claims the benefit of U.S. Provisional Application No. 61/051,900 filed May 9, 2008.

FIELD OF THE INVENTION

The invention relates to improved processes for the etherification of olefins with alcohols in the presence of etherification catalysts.

BACKGROUND OF THE INVENTION

Alkyl ethers of aliphatic alcohols are useful intermediates for a variety of specialty chemical products, including surfactants, chelants, lubricants, and functional additives. The alkyl ethers can be prepared by olefin etherification, also commonly referred to as hydroalkoxylation: an addition reaction of an alcohol to an olefin in the presence of an acid catalyst.

To date, the commercial viability of this process has been limited by low conversion of the olefin to the desired ether due in part to the instability of the ether under the reaction conditions and the tendency of some olefins, particularly aliphatic olefins, to isomerize in the presence of the catalyst and become less reactive. One consequence of this tendency is that the prior art requires the use of large excesses of reactants to achieve even marginal yields. See for example the conversion of 1-dodecene to the dichloro dodecyl ether with 1,3-dichloro-2-propanol described in Bakker et al., J. Am. Oil Chem. Soc., 1967, 44, 517-512.

It would be a significant advance in the field to provide viable olefin etherification processes that overcome the shortcomings of the prior art and in particular that provide high conversion of the starting olefin to desired product.

BRIEF SUMMARY OF THE INVENTION

The invention provides processes for preparing ethers from olefins and alcohols. According to one aspect, the process of the invention comprises: (a) contacting an olefin and an alcohol with a heterogeneous etherification catalyst in a reaction zone under etherification conditions to form an ether compound; (b) removing unconsumed olefin and alcohol, and the ether compound, to a catalyst free zone; (c) repeating steps (a) to (b) using at least a portion of the unconsumed olefin and alcohol until a desired amount of ether compound accumulates in the catalyst free zone; and (d) recovering the ether compound.

According to a second aspect, the process comprises: (a) contacting an olefin with an alcohol in the presence of an etherification catalyst, under etherification conditions, to form an ether compound; (b) recovering the ether compound, and unconsumed alcohol and olefin; (c) using at least a portion of the unconsumed olefin of step (b) in an etherification process conducted according to step (a), wherein the alcohol is a linear or branched alkyl alcohol containing one or two alcohol groups, and further substituted with 1, 2, or 3 activating groups independently selected from CN, $NO_2$, F, Cl, Br, I, $C_1$-$C_6$ alkoxy, and —C(O)O-alkyl.

BRIEF DESCRIPTION OF THE FIGURES

FIG. 1 is a plot comparing the yield of sec-dodecyl 1,3-dichloro-2-propyl ether and isomers based on 1-dodecene intake, as determined by gas chromatography, against reaction time for etherification of dodecene under various etherification conditions.

FIG. 2 is a plot comparing the ratio of the total isomers, other than the main product of 2-chloro-1-(chloromethyl) ethyl 1-methylundecyl ether, in an ether product mixture against reaction time for etherification of dodecene under various etherification conditions.

FIG. 3 is a plot comparing the molar percentage of total internal dodecene isomers in an etherification reaction mixture versus reaction time for etherification of dodecene under various etherification conditions.

DETAILED DESCRIPTION OF THE INVENTION

As noted above, in a first aspect, the invention provides a process for the preparation of ether compounds. The process comprises: (a) contacting an olefin and an alcohol with a heterogeneous etherification catalyst in a reaction zone under etherification conditions to form an ether compound; (b) removing unconsumed olefin and alcohol, and the ether compound, to a catalyst free zone; (c) repeating steps (a) to (b) using at least a portion of the unconsumed olefin and alcohol until a desired amount of ether compound accumulates in the catalyst free zone; and (d) recovering the ether compound.

A principal advantage of the foregoing process is that the ether product is removed from the catalyst while the reaction is ongoing, thus allowing contact between product and catalyst to be limited. As a result, equilibrium driven conversion of ethers back to starting materials, which occurs when ethers are in prolonged contact with catalyst as in prior art processes, is reduced.

A further advantage of the process is that by continuously recycling the mixture of unconsumed olefin and alcohol to the heterogeneous catalyst, conversion to the desired ether product is improved and generally higher than can be achieved with a standard batch reactor system. The process therefore provides a significant cost improvement over existing art.

An additional advantage of the process is that it allows formation of higher yields of ether product without the necessity of using large excesses of starting materials, as in the prior art, thus significantly decreasing raw material costs. In some embodiments, the molar ratio of alcohol to olefin in the process is between about 6:1 and about 1:6, preferably between about 5:1 and 1:5, and even more preferably, between about 3:1 and 1:3, and further preferably between about 2:1 and 1:2. In further preferred embodiments, the alcohol:olefin ratio is less than 6:1, even more preferably, 4:1 or less, and still more preferably 2:1 or less. Particularly preferred is an alcohol to olefin molar ratio of about 1:1.

The zones in the process of the invention permit removal of the ether compound from the heterogeneous catalyst, preferably as it is formed or shortly thereafter, which, as discussed above, mitigates the equilibrium driven conversion of ether compound back to starting materials. There are no particular limitations on what structures are used for the zones. By way of example, multiple reactors appropriately connected for transfer of reactants to the reaction zone may be used, or alternatively, the zones may simply be a single reactor in which the heterogeneous catalyst is isolated out of direct initial contact with reactants.

In laboratory scale syntheses, the first and second zones may be, for instance, a round bottomed flask connected to a soxhlet extractor or distillation column (the reaction zone) in which the heterogeneous catalyst is positioned. A particularly preferred embodiment for laboratory scale synthesis is illustrated by the examples. In this embodiment, a Dean-Stark trap is used as the reaction zone and a round bottomed flask is used as the catalyst free zone.

In another embodiment especially convenient for commercial processing, the reaction zone may be a heated section of pipe or column containing the heterogeneous etherification catalyst through which the olefin and alcohol are passed before being directed or returned to a vessel that is a catalyst free zone.

According to a preferred embodiment of the process of the invention, at least one of the olefin or alcohol starting materials, preferably both, are sourced from the catalyst free zone before being directed to the reaction zone. In this preferred embodiment, the starting materials are directed to the reaction zone preferably by distillation from the catalyst free zone to the reaction zone, where they are condensed on the heterogeneous catalyst. Distillation can be effected by applying heat, reduced pressure, or a combination of heat and reduced pressure, to the catalyst free zone. The temperature and vacuum are chosen depending on the volatility of the alcohol and/or olefin so as to provide distillation thereof. To facilitate condensation on the catalyst surface, the temperature in the reaction zone is preferably lower than the temperature in the catalyst free zone. For example, if the reactants are distilled at a given pressure from the catalyst free zone, e.g., between 60 and 180° C., a heterogeneous catalyst temperature of, for instance, 50 to 150° C. is preferable.

According to a further embodiment, a refluxing solution of the alcohol (e.g., in a suitable solvent) is provided in the catalyst free zone and the olefin is added by controlled addition either to the refluxing alcohol or directly into the reaction zone. Controlled addition of the olefin to the refluxing alcohol is particularly attractive when the olefin has a relative volatility much higher than the alcohol, as it can be used to keep the overall concentration of the olefin at a low enough level to maintain a temperature which allows vaporization of the alcohol. Alternatively, a refluxing solution of the olefin is provided in the catalyst free zone and the alcohol is added by controlled addition either to the refluxing olefin or directly into the reaction zone. Controlled addition of the alcohol to the refluxing olefin is particularly attractive when the alcohol has a relative volatility much higher than the olefin, as it can be used to keep the overall concentration of the alcohol at a low enough level to maintain a temperature which allows vaporization of the olefin. For very low boiling olefins or alcohols, contact with the heterogeneous catalyst may be carried out under pressure to ensure the material remains in the liquid phase.

Upon formation of the ether compound or shortly thereafter, the ether compound, and unconsumed olefin and alcohol are removed and directed to the catalyst free zone which, according to a preferred embodiment, already contains alcohol or olefin, or preferably both, starting materials. Because the alcohol and olefin generally have a lower boiling point than the ether product, they can be re-distilled from the catalyst free zone to the reaction zone to form further ether compound, whereas the already formed ether compound accumulates in the catalyst free zone, out of contact with the heterogeneous catalyst, thus allowing the process to proceed unencumbered by equilibrium reaction reversal of the already formed ether compound. The temperature in the catalyst free zone may be increased and/or the vacuum decreased as the reaction progresses in order to maintain distillation rate.

The contacting of the alcohol and olefin with the heterogeneous catalyst, removal to a catalyst free zone (together with formed ether compound), and then retransfer to the reaction zone is repeated until the desired amount of ether compound accumulates in the catalyst free zone. Practically, the process may be continued until the concentration of unconsumed alcohol and olefin is so low that that they cannot be efficiently separated from the ether product in the catalyst free zone under the conditions of the process. The process may, however, be terminated earlier simply by ceasing the repetition of the steps. In some preferred embodiments, an ether compound yield, based on the olefin, of at least 60%, more preferably at least 70%, and even more preferably at least 80%, is considered a desired amount of ether compound.

Once the desired amount of ether compound is accumulated, the mixture in the catalyst free zone (containing the product) is removed for use or further processing. In some applications, the ether product can be utilized without purification. Alternatively, the ether product can be readily purified by techniques well known to those skilled in the art, such as high efficiency distillation.

Examples of preferred heterogeneous etherification catalysts for use in this first aspect of the invention include, but are not limited to, acidic ionic exchange resins, such as DOWEX DR-2030 available from The Dow Chemical Company, clays, zeolites, sulfonated polystyrene beads, and acids immobilized on a heterogeneous surface, such as tetrafluoroethane-sulfonic acid on silica beads. The ratio of catalyst to reactants is not critical and is generally adjusted so as to obtain a desired reaction rate. Preferably, the catalyst is at a temperature of between about 50 and 150° C. during the process in order to facilitate the etherification reaction.

Alcohols that can be used in the process are preferably short chain linear or branched alkyls (e.g., containing 2-6 carbons, more preferably 2-4 carbons) substituted with one or two alcohol groups, preferably one alcohol group, and further substituted with 1, 2, or 3 activating groups independently selected from CN, $NO_2$, F, Cl, Br, I, $C_1$-$C_6$ alkoxy, and —C(O)O-alkyl. The alcohol should distill readily without excessive decomposition.

In a preferred embodiment, the alcohol is a compound of the following formula (I):

wherein $R^4$ is H, $CH_3$, X, $CH_2X$, $CHX_2$, $CX_3$, CN, or $CH_2OR^5$;

A is CN, $CH_2OR^5$, $CH_2X$, $CHX_2$, $CX_3$, $CH_2CH_2X$, $CHXCH_2X$, $CHXCH_2OH$, $CH(OH)CH_2X$, $CH_2OH$, or —C(O)$OR_5$;

X is $NO_2$, F, Cl, Br, or I; and $R^5$ is $C_1$-$C_6$ alkyl.

Preferred alcohols of the formula (I) include those wherein $R^4$ is H, $CH_3$, or $CH_2X$. Further preferred are alcohols wherein A is $CH_2X$, $CHXCH_2OH$, or $CH_2OH$, with it being further preferred that when A is $CH_2OH$, $R^4$ is not H and is preferably $CH_2X$. Preferred X in the above formula is halogen and more preferably chloro.

It is further preferred that the compound of formula (I) contain at least one CN or X group.

Particularly preferred alcohols include: 1,3-dichloro-2-propanol, 2,3-dichloropropanol, 2-chloroethanol, 2-chloro-1,3-propanediol, 3-chloro-1,2-propanediol, or a mixture of two or more thereof.

Olefins that can be used in the process of the first aspect of the invention are generally those that are distillable under the process conditions, lack basic functionality capable of quenching the heterogeneous catalyst (which is generally acidic), and react with the activated alcohol to form ethers with limited loss of yield to higher molecular weight polyolefins or other unwanted by-products. Examples include, for instance, linear or branched alkenes such as alpha-olefins, internal disubstituted olefins, or cyclic structures (e.g., $C_3$-$C_{12}$ cycloalkene). Examples further include: butene, pentene, hexene, methylpentene, heptene, octene, nonene, decene, undecene, dodecene, tridecene, tetradecene, pentadecene, hexadecene, heptadecene, octadecene, nonadecene, and eicosene.

Particularly suitable are linear or branched alpha-olefins (i.e., 1-alkenes) containing 3 to 22 carbon atoms, or a mixture of isomers of linear or branched 1-alkenes containing 3 to 22 carbon atoms together with their internal and/or tertiary olefin isomers. More preferably, the alkenes are linear or branched (preferably linear) and contain 3 to 18, and even more preferably 3 to 16, carbon atoms. Non-limiting examples of particularly preferred alpha olefins include: 1-butene, 1-pentene, 1-hexene, 4-methyl-1-pentene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, or mixtures of two or more thereof.

As the olefin is isomerized by contacting the acidic catalyst, it is not necessary to use an alpha-olefin, and internal olefins containing 4 to 22 carbon atoms, or mixtures of isomers of linear or branched alkenes are also suitable for use. Non-limiting examples of suitable internal olefins include: 2-butene, 2-pentene, 2-hexene, 3-hexene, 2-heptene, 3-heptene, 2-octene, 3-octene, 4-octene, 2-nonene, 3-nonene, 4-nonene, 2-decene, 3-decene, 4-decene, 5-decene, etc, or mixtures of two or more thereof.

In its second aspect, the invention provides an etherification process that is suitable for use with both heterogeneous and homogeneous etherification catalysts and, in its preferred embodiment, is particularly advantageous for the etherification of linear or branched 1-alkenes (alpha-olefins). This aspect of the invention also offers significant process and cost improvement over the existing art for olefin etherification. The improvements are achieved primarily by use of the particular alcohols described herein and by the recycling of unconsumed olefins (i.e., unreacted olefins and/or olefin isomers thereof).

The process of the second aspect comprises: (a) contacting an olefin with an alcohol in the presence of an etherification catalyst, under etherification conditions, to form an ether compound; (b) recovering the ether compound, and unconsumed alcohol and olefin; (c) using at least a portion of the unconsumed olefin of step (b) in an etherification process conducted according to step (a), wherein the alcohol is a linear or branched alkyl alcohol (e.g., containing 2-6 carbons, more preferably 2-4 carbons) containing one or two alcohol groups, preferably one alcohol group, and further substituted by 1, 2, or 3 activating groups independently selected from CN, $NO_2$, F, Cl, Br, I, $C_1$-$C_6$ alkoxy, and —C(O)O-alkyl.

Suitable catalysts for the process of the second aspect of the invention include Bronsted acids such as triflic (trifluoromethanesulfonic) acid, methanesulfonic acid, or sulfuric acid, Lewis acids such as $BF_3$ and its derivatives (e.g., dihydrate or ether), trimethylsilyl triflate, and acidic ionic exchange resins, such as DOWEX DR-2030 available from The Dow Chemical Company). In some embodiments, the catalyst is preferably triflic acid or trimethylsilyl triflate. Unlike $BF_3$ or its derivatives (which is preferred in the alpha olefin embodiment described below), triflic acid and trimethylsilyl triflate have surprisingly been found to effectively catalyze the reaction of internal olefins, and thus improve overall olefin conversion to ethers. These catalysts are also more effective than conventional catalysts and therefore allow the process to run effectively at lower catalyst concentrations.

Preferred alcohols for use in the second aspect are those of formula (I) as defined above. Preferred alcohols of formula (I) include compounds wherein $R^4$ is H, $CH_3$, or $CH_2X$. Further preferred are compounds wherein A is $CH_2X$, $CHXCH_2OH$, or $CH_2OH$, with it being further preferred that when A is $CH_2OH$, $R^4$ is not H and is preferably $CH_2X$. Preferred X in formula (I) is halogen and more preferably chloro. Also preferably are alcohols wherein the compound contains at least one CN or X group.

Particularly preferred alcohols include: 1,3-dichloro-2-propanol, 2,3-dichloropropanol, 2-chloroethanol, 2-chloro-1,3-propanediol, 3-chloro-1,2-propanediol, or a mixture of two or more thereof.

Olefins suitable for use in the second aspect of the invention are generally those that are distillable under the process conditions, lack basic functionality capable of quenching the heterogeneous catalyst (which is generally acidic), and react with the activated alcohol to form ethers with limited loss of yield to higher molecular weight polyolefins or other unwanted by-products. Examples include, for instance, linear or branched alkenes such as alpha-olefins, internal disubstituted olefins, or cyclic structures (e.g., $C_3$-$C_{12}$ cycloalkene).

The catalyst concentration in the process is preferably from 0.01 mol % to 20 mol %, more preferably from 0.1 mol % to 10 mol %, most preferably from 0.25 mol % to 5 mol %, based on the olefin. The olefin to alcohol molar ratio in the reaction may vary. The olefin can be used in excess, the alcohol can be used in excess, or the reagents can be mixed in stoichiometric amounts. The separation and recycle strategy is adjusted accordingly. In some embodiments, the molar ratio of olefin to alcohol is preferably between 20 and 0.05, more preferably between 10 and 0.1, and even more preferably between 6 and 0.16.

The process is preferably run at elevated temperature, such as between 60° C. and 150° C. The process may be carried out under vacuum, atmospheric or elevated pressure. Reaction time is preferably between about 5 minutes and 24 hours, but can vary depending upon equipment size and reactants and catalyst used.

In a preferred embodiment, the olefin of step (a) of the second aspect process is a linear or branched 1-alkene (alpha olefin) containing 3 to 22 carbon atoms, more preferably 3 to 18 carbon atoms, and even more preferably 3 to 16 carbon atoms. Examples include 1-butene, 1-pentene, 1-hexene, 4-methyl-1-pentene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, and mixtures of two or more thereof. The preferred etherification catalyst under this embodiment is $BF_3$ or a derivative thereof. Generally, upon exposure to an acidic catalyst, an alpha-olefin isomerizes to an equilibrium mixture of terminal and internal alkenes. Because, under the conditions of this preferred embodiment, the terminal alpha olefin is generally more reactive than its internal isomers to etherification, the unreacted olefin of step (b) of the process is depleted of alpha-olefin and enriched with internal olefins. Using at least a portion of this unreacted olefin (e.g., at least 25 weight %, more preferably at least weight 50%, and even more preferably 100 weight %) in an etherification process conducted as described in step (a) (e.g., in a subsequent etherification reaction) has surprisingly been found to pre-establish the equilibrium mixture without expending the alpha-olefin of the alpha-olefin charge to further internal isomers. Advantageously, therefore, the reaction mixture in the latter etherification remains enriched in alpha-olefin. As a result, the yield of alkyl ether product based on alpha-olefin charged to the reactor is increased as compared to processes that do not utilize the re-use step. According to this preferred embodiment, the molar ratio of the total isomers in the isomer mixture to the alpha-olefin is between 0.05 and 10, preferably between 0.1 and 3, and more preferably between 0.2 and 2.

Various methods can be used for recovering the ether compound and unconsumed olefins of step (b) from the reaction. For instance, in an extraction method, a non-polar solvent is used to extract the ether products and unconsumed olefins from unreacted alcohol and from the catalyst. The extracted mixture may then be distilled to separate the product from the unconsumed olefins. The recovered olefins are recycled to the same or, preferably, to a subsequent reaction, as described above. Preferred non-polar solvents for the extraction include, but are not limited to, pentane, heptane, hexanes, toluene, and the like. If appropriately selected, e.g., with the addition of minor amounts of water, the non-polar solvent may also promote phase separation of the unreacted alcohol and/or the catalyst in the extracted mixture, allowing for easy separation and optional reuse of these components.

Another method for separating the ether product and the unconsumed olefins from the reaction mixture is through direct distillation of the reaction mixture. Optionally, the catalyst is quenched or adsorbed onto a basic solid or resin before distillation. Three fractions are collected from the distillation: unreacted alcohol, unconsumed olefin, and the ether product. The recovered alcohol may be reused.

Preferred ether compounds prepared by the processes of the first or second aspect of the invention are of the following formula:

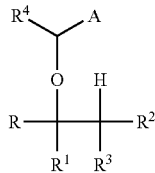

wherein R is linear or branched $C_2$-$C_{22}$ alkyl;

$R^1$, $R^2$, and $R^3$ are independently H or linear or branched $C_1$-$C_{18}$ alkyl each of which is optionally independently substituted with 1, 2, or 3 non-basic groups, such as siloxanes, alkyl ethers, acetals, and acetates;

$R^4$ is H, $CH_3$, X, $CH_2X$, $CHX_2$, $CX_3$, CN, or $CH_2OR^5$;

A is CN, $CH_2OR^5CH_2X$, $CHX_2$, $CX_3$, $CH_2CH_2X$, $CHXCH_2X$, $CHXCH_2OH$, $CH(OH)CH_2X$, $CH_2OH$, or $COOR^5$;

X is $NO_2$, F, Cl, Br, or I; and $R^5$ is $C_1$-$C_6$ alkyl.

Further preferred compounds of the foregoing formula are those wherein the compound contains at least one CN or at least one X group.

Also preferred are compounds where $R^1$, $R^2$, and $R^3$ are each hydrogen.

Further preferred are compounds where $R^4$ is H, $CH_3$ or $CH_2X$, particularly $CH_2Cl$.

Also preferred are compounds where A is $CH_2X$, particularly $CH_2Cl$.

Various steps of the processes of the invention may optionally be run in a solvent. The solvent should not react with the olefin, alcohol or catalyst or initiate any undesirable side-reactions. Examples of suitable solvents include, but are not limited to toluene, xylene, tetrahydrofuran, diglyme, dioxane, dialkyl ethers (e.g., diethyl ether), chloroform, methylene chloride and the like. In the second aspect of the invention, if the olefin and the alcohol are immiscible at the desired reaction temperature, it is advantageous to use a solvent that makes the system one phase.

The olefins of the first and second aspect of the invention are optionally substituted with 1, 2, or 3 independently selected substituents. The substituent should be substantially unreactive towards the catalysts and alcohol. Examples of such groups include: non-basic groups such as siloxanes, alkyl ethers, acetals, or acetates. The groups may be located at any available position on the olefin (e.g., allylic, homo-allylic, or more distant functionality).

The product ether compounds are useful in a variety of applications, or are intermediates for the manufacture of downstream products useable in various applications, including as surfactants, chelants, lubricants, and functional additives.

The following examples are illustrative of the invention but are not intended to limit its scope.

EXAMPLES

Example I-1

Comparative

Reaction of 1-Dodecene and
1,3-Dichloro-2-propanol Using
Trifluoromethanesulfonic Acid A 1-L round-bottom flask is charged with 206.5 g (1.60 mol) of 1,3-dichloro-2-propanol ("DCP"), 1.32 g of trifluoromethanesulfonic (triflic) acid, and reacted at 80 to 85° C. with 271.8 g (1.62 mol) of 1-dodecene, added in approximately 50-g portions over 6 hours. GC analysis of the final reaction product finds 25.9 wt % 1,3-dichloro-2-propanol, 33.6 wt % of dodecene (mixture of isomers), and 37.1 wt % of the 1,3-dichloropropyl ether of dodecane (mixture of positional isomers). The cooled reaction mixture (479.6 g) is added to 3.5 g of sodium carbonate and 10 g sodium chloride in 100 g of water. The top layer (399.58 g), containing 35.0 wt %, (or 171.1 g) of the 1,3-dichloropropyl ether of dodecane (mixture of positional isomers) is removed and a 360.2 g portion purified by distillation to afford 139.1 g of the 1,3-dichloropropyl ether of dodecane (mixture of positional isomers) (b.p. 135-140° C. at 1 torr).

Example I-2

Comparative

Reaction of 1-Dodecene and
1,3-Dichloro-2-propanol Using Methanesulfonic
Acid

A 1-L round-bottom flask is charged with 173 g (1.34 mol) of 1,3-dichloro-2-propanol, 15.96 g of methanesulfonic acid, and reacted at 80 to 85° C. with 226.6 g (1.34 mol) of 1-dodecene, added in 2 portions, and held overnight at temperature. GC analysis of the final reaction product finds 27.3 wt % 1,3-dichloro-2-propanol, 34.8 wt % of dodecene (mixture of isomers), and 32.8 wt % of the 1,3-dichloropropyl ether of dodecane (mixture of positional isomers).

Example I-3

Comparative

Etherification of 1-Dodecene Using DOWEX DR-2030 Resin

A 100-mL round bottom flask is charged with 0.92 g of DOWEX DR-2030 resin, 7.90 g (0.061 mol) of 1,3-dichloro-2-propanol, and 10.36 g (0.062 mol) of 1-docenene. The mixture is warmed to 80 to 100° C. for 2 hours. GC analysis of the solution finds 28.4 wt % 1,3-dichloro-2-propanol, 41.8 wt % of dodecene (mixture of isomers), and 26.6 wt % of the 1,3-dichloropropyl ether of dodecane (mixture of positional isomers). After holding overnight at 100° C., GC analysis of the solution finds 35.0 wt % 1,3-dichloro-2-propanol, 44.9 wt % of dodecene (mixture of isomers), and 21.8 wt % of the 1,3-dichloropropyl ether of dodecane (mixture of positional isomers).

Example I-4

Illustrating Aspect One of the Invention

Etherification of 1-Dodecene with 1,3-Dichloro-2-propanol Under Reactive Distillation Conditions A bottom-drain Dean-Stark trap with a glass wool plug to retain the resin beads is charged with 16.2 g of DOWEX DR-2030 resin, the resin is wetted with 11.5 g of 1,3-dichloro-2-propanol, and the apparatus attached to a 1-L round bottom flask. The flask is charged with 196 g (1.1 mol) of 1-dodecene and 139.7 g of 1,3-dichloro-2-propanol (total of 1.17 mol). Vacuum (30-40 torr) is applied, and the 1-L flask heated to distill at a bottoms temperature of 90-95° C. The temperature in the Dean Stark trap is controlled at 80 to 90° C. (e.g., with a temperature controlled heating mantle). Distillate from the 1-L flask is condensed into the Dean Start trap containing the warmed resin, and returned to the 1-L flask. The temperature in the 1-L flask climbs to 133° C. with continued distillation. GC analysis of the cooled reaction mixture (after about 20 hours of reaction time) finds 2 wt % 1,3-dichloro-2-propanol, 11.8 wt % of dodecene (mixture of isomers), and 85 wt % of the 1,3-dichloropropyl ether of dodecane (mixture of positional isomers). A 297.46-g portion of the reaction mixture is purified by distillation to afford 222.5 g of the 1,3-dichloropropyl ether of dodecane (mixture of positional isomers) (b.p. 123° C. at 0.7 torr).

Example I-5

Illustrating Aspect One of the Invention

Etherification of 1-Decene with 1,3-Dichloro-2-propanol Under Reactive Distillation Conditions A bottom-drain Dean-Stark trap with a glass wool plug to retain the resin beads is charged with 19 g of DOWEX DR-2030 resin, the resin is wetted with 50 g of 1,3-dichloro-2-propanol, and the apparatus attached to a 2-L round bottom flask. The flask is charged with 319.9 g (2.28 mol) of 1-decene and 243.1 g of 1,3-dichloro-2-propanol (total of 2.26 mol). Vacuum (40-50 torr) is applied, and the 2-L flask is heated to distill at an initial bottoms temperature of 88° C. The temperature in the Dean Stark trap is controlled at 80 to 90° C. Distillate from the 2-L flask is condensed into the Dean Start trap containing the warmed resin, and returned to the 2-L flask. The temperature in the 2-L flask climbs to 146° C. with continued distillation. After about 20 hours of reaction time, GC analysis of the cooled reaction mixture finds 2 wt % 1,3-dichloro-2-propanol, 6.7 wt % of decene (mixture of isomers), and 93 wt % of the 1,3-dichloropropyl ether of decane (mixture of positional isomers). A 539.57 g portion of the reaction mixture is purified by distillation to afford 452.7 g of the 1,3-dichloropropyl ether of decane (mixture of positional isomers)(b.p. 101° C. at 0.7 torr).

Example I-6

Comparative

Etherification of 1-Dodecene in the Presence of Tetrafluoroethanesulfonic Acid on Porous Silica Solid Phase Catalyst A 100-mL round bottom flask is charged with 0.44 g of tetrafluoroethanesulfonic acid on porous silica (DuPont), 8.88 g (0.069 mol) of 1,3-dichloro-2-propanol, and 11.48 g (0.068 mol) of 1-docenene. The mixture is warmed to 80° C. for 1 hour. GC analysis of the solution finds 35.1 wt % 1,3-dichloro-2-propanol, 45.3 wt % of dodecene (mixture of isomers), and 26.8 wt % of the 1,3-dichloropropyl ether of dodecane (mixture of positional isomers). After holding overnight at 80° C., GC analysis of the solution finds 26.3 wt % 1,3-dichloro-2-propanol, 31.6 wt % of dodecene (mixture of isomers), and 37.8 wt % of the 1,3-dichloropropyl ether of dodecane (mixture of positional isomers)

Example I-7

Illustrating Aspect One of the Invention

Etherification of 1-Dodecene with 1,3-Dichloro-2-propanol Under Reactive Distillation Conditions Using Tetrafluoroethanesulfonic Acid on Porous Silica Solid Phase Catalyst A bottom-drain Dean-Stark trap with a glass wool plug to retain the resin beads is charged with 1.15 g of tetrafluoroethanesulfonic acid on porous silica (DuPont) and the apparatus attached to a 1-L round bottom flask. The flask is charged with 136 g (0.81 mol) of 1-dodecene and 109.8 g of 1,3-dichloro-2-propanol (0.85 mol). Vacuum (25-30 torr) is applied, and the 1-L flask heated to distill at a pot temperature of 80-85° C. The temperature in the Dean Stark trap is controlled at 80 to 90° C. Distillate from the 1-L flask is condensed into the Dean Start trap containing the warmed resin, and returned to the 1-L flask. The temperature in the 1-L flask climbs to 93° C. with continued distillation. After about 20 hours of reaction time, GC analysis of the cooled reaction mixture finds 17.3 wt % 1,3-dichloro-2-propanol, 34.3 wt % of dodecene (mixture of isomers), and 45.8 wt % of the 1,3-dichloropropyl ether of dodecane (mixture of positional isomers).

Example I-8

Illustrating Aspect One of the Invention

Etherification of 1-Octene with
1,3-Dichloro-2-propanol Under Reactive Distillation
Conditions A 2-L round-bottom flask with a magnetic stirrer is fitted into a heating mantle. Distillate from the 2-L flask is condensed into a side arm distillate receiver containing a magnetic stirrer and temperature probe. A valved line between the distillate receiver and the 2-L flask gives a nominal volume of about 100 mL in the distillate receiver. Liquid is pumped from the bottom of the distillate receiver though a 18 inch long ½ inch diameter stainless steel tube. The tube is fitted on each end with 140 µm screen filters to provide a catalyst bed containing approximately 15 g of DOWEX DR-2030 ion exchange resin. The ½ inch tube is jacketed for a length of 9 inches; the jacket system is heated using a recirculating hot oil bath. The outlet from the catalyst bed returns liquid to the distillate receiver. A 250-mL addition funnel attached to an addition pump allows for a constant rate of component addition. The 2-L vessel is charged with 665.89 g (5.16 mol) of 1,3-dichloro-2-propanol. The vacuum is adjusted to 18 to 20 torr, and the 2-L vessel heated to afford distillation at an initial temperature of 81° C., with a vapor temperature of 75° C. The catalyst bed oil bath is set to 130° C. to give a temperature in reaction product exiting the catalyst bed of 80-91° C. The condenser temperature is 0 to −6° C. The distillate receiver temperature is 35 to 45° C. A total of 634.21 g (5.65 mol) of 1-octene is added over the course of the reaction using the addition pump. The temperature in the 2-L vessel rises to 123° C. and the overhead temperature rises to 87° C. GC analysis of the cooled reaction mixture finds 9.8 wt % of DCP, 1.1 wt % of octenes, and 73.5 wt % of the DCP ether of octane. The solution in the distillate receiver and catalyst bed (79.65 g, 6.1% of mass loaded) is discarded. The solution in the 2-L vessel (926.3 g, 71.2% of mass loaded) is loaded to a 2-L round-bottom flask and purified by distillation at 1 to 2 torr using a 14" vacuum-jacketed Vigreux column topped with a reflux splitter. The first fraction (108 g) is collected using a 2:1 reflux ratio at an overhead temperature of 20 to 80° C. with a bottoms temperature of 60-130° C. The product fraction is collected using a 3:1 reflux ratio at an overhead temperature of 85° C. and a bottoms temperature of 142° C. to afford 785.31 g (3.26 mol) of the 1,3-dichloropropyl ether of octane (1,3-dichloropropan-2-lyoxyoctane, mixture of positional isomers, 85% distilled yield).

Example I-9

Illustrating Aspect One of the Invention

Etherification of 1-Tetradecene with
1,3-Dichloro-2-propanol Under Reactive Distillation
Conditions The equipment of Example I-8 is used for this example. The 2-L vessel is charged with 43.13 g (0.334 mol) of 1,3-dichloro-2-propanol and 458.76 g (2.34 mol) of 1-tetradecene. The vacuum is adjusted to 18 to 20 torr, and the 2-L vessel is heated to afford distillation at an initial temperature of 138° C., with a vapor temperature of 120° C. The catalyst bed oil bath is set to 130° C. to give a temperature in reaction product exiting the catalyst bed of 80-95° C. The condenser temperature is 0 to −5° C. The distillate receiver temperature is 50 to 70° C. An additional 372.53 g (2.89 mol) of 1,3-dichloro-2-propanol is added using the addition pump. The temperature in the 2-L vessel rises to 170° C. GC analysis of the cooled reaction mixture finds approximately 3 wt % of tetradecenes, and 97 wt % of the DCP ether of tetradecane. The solution in the distillate receiver and catalyst bed (122.1 g, 14% of mass loaded) is discarded. The solution in the 2-L vessel (684.77 g, 78.3% of mass loaded) is loaded to a 2-L round-bottom flask and purified by distillation at 0.2 to 1 torr using a 14" vacuum-jacketed Vigreux column topped with a reflux splitter. The first fraction (22.45 g) is collected using a 2:1 reflux ratio at an overhead temperature of 20 to 90° C. with a bottoms temperature of 103-212° C. The product fraction is collected using a 5:1 reflux ratio at an overhead temperature of 133° C. and a bottoms temperature of 221° C. to afford 629.66 g (1.93 mol) of the 1,3-dichloropropyl ether of tetradecane (1,3-dichloropropan-2-lyoxytetradecane, mixture of positional isomers, 92% distilled yield).

Example II-1

Comparative

Etherification of 1-Dodecene and Extraction with
Heptane

To a 1000 ml round bottom flask equipped with condenser, overhead stirrer, and nitrogen inlet system is added 528 g of 1,3-dichloro-2-propanol, 6.6 g of $BF_3$ dihydrate, and 103 g of 1-dodecene at room temperature. The mixture is heated to 95° C. for 6 hours. The reaction mixture is cooled to room temperature and is then transferred to a 1000 ml separation funnel; 200 ml of heptane is added and two phases are separated. The lower phase (containing excess dichloropropanol, ether products, unreacted and isomerized olefins, and the catalyst) is extracted with 200 ml of heptane three more times. The heptane solutions are combined and the heptane is removed on a rotary evaporator. Distillation of residual heptane under reduced pressure affords 46.3 g of dodecene isomers mixture and 94.4 g of sec-dodecyl 1,3-dichloro-2-propyl ether and isomers. The dodecene mixtures is collected at 80-105° C./0.6 mmHg, and the ether product is collected as 128-141° C./0.6 mmHg)

Example II-2

Comparative

Etherification of 1-Dodecene with
1,3-Dichloro-2-Propanol

To a 250 ml round bottom flask is charged 35.25 g of 1,3-dichloro-2-propanol (273.3 mmoles), 0.51 ml of $BF_3$ diethylether and 6.74 g of 1-dodecene (40 mmoles) at room temperature. The reaction mixture is heated to 95° C. and the reaction monitored by gas chromatography The yield of sec-dodecyl 1,3-dichloro-2-propyl ether and isomers based on 1-dodecene intake, determined by gas chromatography, against reaction time is plotted in FIG. 1. It is shown that the yield goes through a maximum at about 61 mol % and then drops back to ~50 mol %. The ratio of the total isomers other than the main product of 2-chloro-1-(chloromethyl)ethyl 1-methylundecyl ether (i.e., the isomers of the ether product with the ether linkage other than at C-2 position) among the ether product mixture in the reaction mixture is plotted against reaction time in FIG. 2. The isomers (other than of 2-chloro-1-(chloromethyl)ethyl 1-methylundecyl ether) amount in the product mixture keeps increasing with the reaction time.

Figure 3:
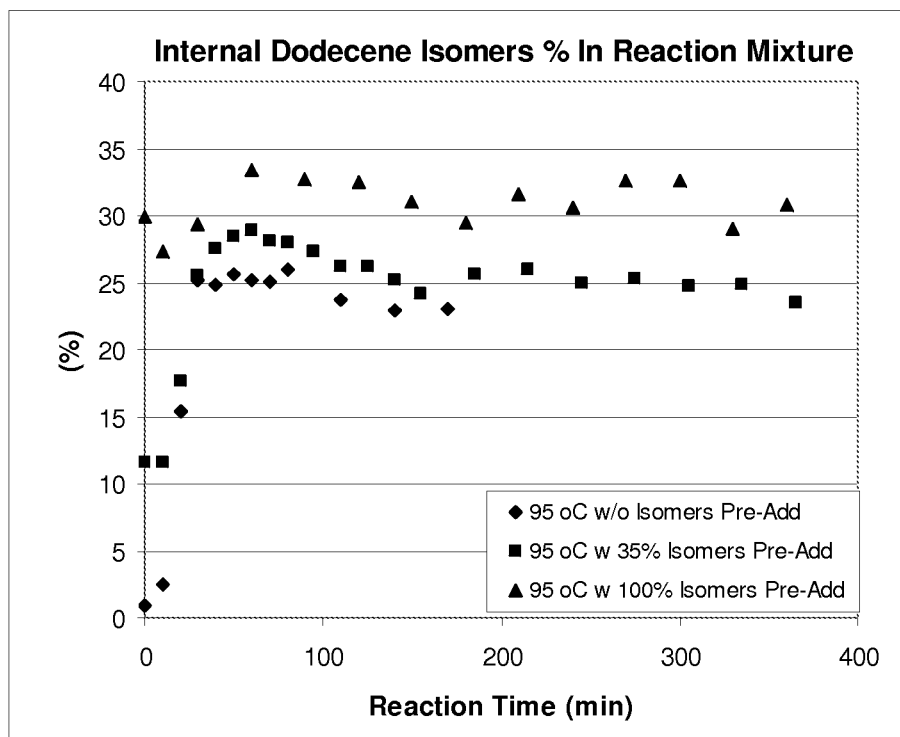

Excluding 1,3-dichloro-2-propanol, the molar percentage of the total internal dodecene isomers in the reaction mixture is plotted versus reaction time in FIG. 3. The total internal olefin isomers percentage increases from less than 1% at the beginning of the reaction to about 25% corresponding to the time at which the ether yield reaches the maximum. The result indicates that about 25% of the 1-dodecene is converted to internal olefin isomers during the reaction.

Example II-3

Example of the Invention

Etherification of 1-Dodecene with
1,3-Dichloro-2-Propanol and Addition of Portion of
Olefin Isomers (1:0.35 Molar Ratio)

The reaction in Example II-2 is repeated with the addition of the dodecene isomers mixture obtained in Example 1 at the molar ratio of 1-Dodecene:Dodecene Isomers Mixture=1:0.35. The reaction is monitored by gas chromatography.

The yield of sec-dodecyl 1,3-dichloro-2-propyl ether and isomers based on 1-dodecene intake, determined by gas chromatography, is compared with the results of Example II-2 in FIG. 1. The ether yield based on 1-dodecene intake is increased to over 70 mol % and the yield only slightly drops back after reaching the maximum value.

Figure 2:
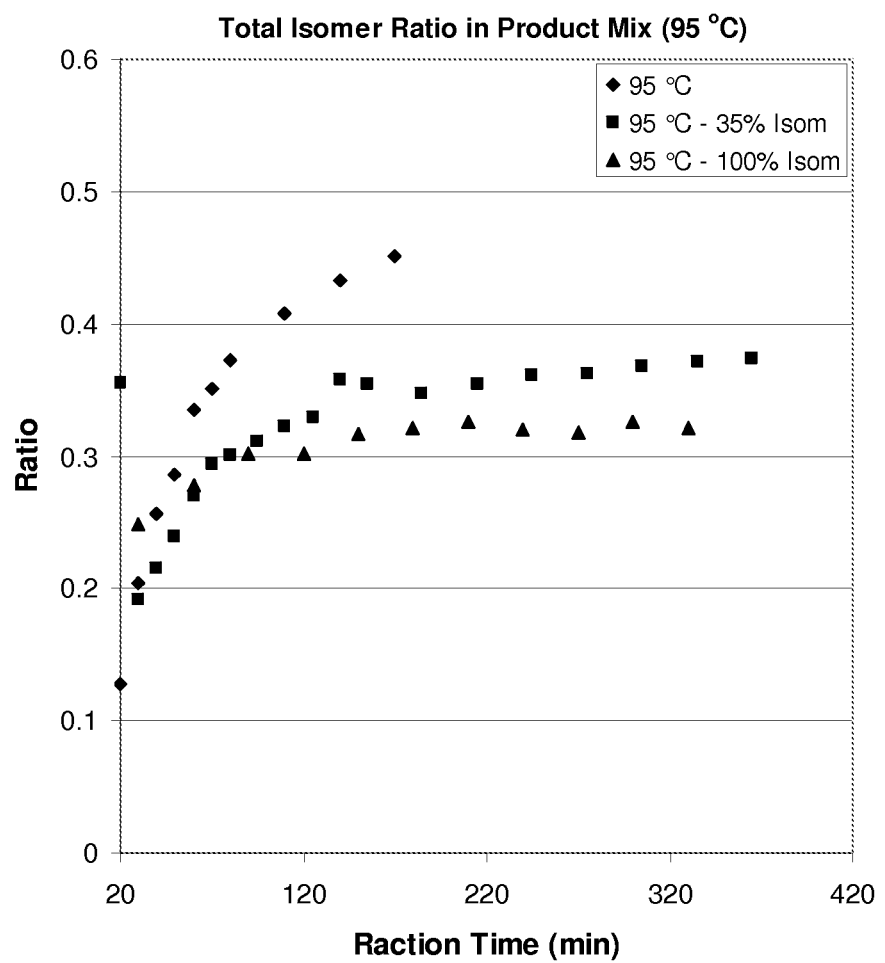

The ratios of the total isomers other than the main product of, 2-chloro-1-(chloromethyl)ethyl 1-methylundecyl ether among the ether product mixture in the reaction mixture versus reaction time is compared in FIG. 2 with the results of Example II-2. The isomer amounts in the product mixture is smaller than those in Example II-2 and the change with reaction time after reaching the maximum yield (refer to FIG. 1) is smaller than that observed in Example II-2.

Excluding 1,3-dichloro-2-propanol, the molar percentage of the total internal dodecene isomers in the reaction mixture versus reaction time is compared with Example II-2 in FIG. 3. The total internal olefin isomers percentage increases from ~12% at the beginning of the reaction to about 29% at the point where maximum ether yield is reached (refer to FIG. 1). The result indicates that about 17% of the 1-dodecene is converted to internal olefin isomers during the reaction.

Example II-4

Etherification of 1-Dodecene with
1,3-Dichloro-2-Propanol and Addition of Olefin
Isomers (1:1 Molar Ratio)

The reaction of Example II-2 is repeated with the addition of the dodecene isomers mixture obtained in Example II-1 at the molar ratio of 1-Dodecene:Dodecene Isomers Mixture=1:1. The reaction is monitored by gas chromatography.

The yield of sec-dodecyl 1,3-dichloro-2-propyl ether and isomers based on 1-dodecene intake, determined by gas chromatography, is compared with the results of Examples II-2 and II-3 in FIG. 1. The ether yield based on 1-dodecene intake is increased to approximately 90 mol % and the yield is stable after reaching the maximum value.

The ratios of the total isomers other than the main product of, 2-chloro-1-(chloromethyl)ethyl 1-methylundecyl ether among the ether product mixture in the reaction mixture versus reaction time is compared with the results of Examples II-2 and II-3 in FIG. 2. The isomer amounts in the product mixture are smaller than those in Examples II-2 and II-3 and stay stable with reaction time after reaching the maximum yield (refer to FIG. 1).

Excluding 1,3-dichloro-2-propanol, the molar percentage of the total internal dodecene isomers in the reaction mixture versus reaction time is compared with Examples II-2 and II-3 in FIG. 3. The total internal olefin isomers percentage maintains around 30% through the course of the reaction. The result indicates that there is no significant amount of 1-dodecene converted to internal olefin isomers during the reaction.

Example II-5

Etherification of 1-Dodecene and Extraction with
Heptane

To a 1000 ml round bottom flask equipped with condenser, overhead stirrer, and nitrogen inlet system is added 526.2 g of 1,3-dichloro-2-propanol, 7.8 ml of boron trifluoride diethyl etherate, and 101 g of 1-dodecene at room temperature. The mixture is heated to 95° C. for 1 hour. The reaction mixture is cooled to room temperature and then transferred to a 1000 ml separation funnel. 200 ml of heptane is added and two phases are separated. The lower phase containing the excess dichloropropanol, ether products, unreacted and isomerized olefins, and the catalyst is extracted with 200 ml of heptane three more times. The heptane solutions are combined and heptane is removed on a rotary evaporator. Distillation under reduced pressure affords 46.3 g of dodecene isomers mixture and 91.6 g of sec-dodecyl 1,3-dichloro-2-propyl ether and isomers. Yield=51.3% (based on 1-dodecene).

Example II-6

Etherification of 1-Dodecene with
1,3-Dichloro-2-Propanol and Addition of Olefin
Isomers (1:1 Molar Ratio)

To a 1000 ml round bottom flask equipped with condenser, overhead stirrer, and nitrogen inlet system is added 526.2 g of 1,3-dichloro-2-propanol, 7.8 ml of boron trifluoride diethyl etherate, 101 g of 1-dodecene, and 101 g of the olefin isomer mixture obtained from a previous run such as Example II-5 at room temperature. The mixture is heated to 95° C. for 1 hour. The reaction mixture is cooled to room temperature and is then transferred to a 1000 ml separation funnel; 200 ml of heptane are added and two phases are separated. The lower phase is extracted with 200 ml of heptane three more times. The heptane solutions are combined and heptane is removed on a rotary evaporator. Distillation under reduced pressure affords 85.1 of dodecene isomers mixture and 171.2 g of sec-dodecyl 1,3-dichloro-2-propyl ether and isomers. Yield=96% (Based on 1-dodecene). The $^{13}C$ NMR spectrum is collected. The component ratio corresponding to the C-2, C-3, and higher C linked ethers is determined from the area integration of the peaks as 64:20:16.

Catalyst Screening Examples

Catalyst screening is carried out in a set of 48 high throughput reactors (cells) under nitrogen atmosphere. The reagents are transferred using a standard automated liquid handling system while the catalyst solutions are charged manually. Each cell is equipped with a glass liner and stirrer.

Olefin, alcohol, and catalyst are mixed (n-hexadecane is added as an internal standard) under nitrogen atmosphere and agitated for 3 hours at 80° C. After cooling, THF is added and the solution analyzed by GC to determine ether product yield for all isomers. Data are shown in Table 1 below. In Table 1, DCP refers to 1,3-dichloro-2-propanol.

TABLE 1

| Ex. | Olefin (mmol) | Alcohol (mmol) | Catalyst (mmol) | Product Yield |
|---|---|---|---|---|
| II-7 | 1-Dodecene (17 mmol) | DCP (3 mmol) | Triflic Acid (0.2 mmol) | 67% |
| II-8 | 1-Dodecene (17 mmol) | DCP (3 mmol) | trimethyl silyl triflate (0.2 mmol) | 63% |
| II-9 | 1-Dodecene (17 mmol) | DCP (3 mmol) | boron trifluoride etherate (0.2 mmol) | 38% |
| II-10 | 1-Dodecene (10 mmol) | DCP (10 mmol) | Triflic Acid (0.2 mmol) | 40% |
| II-11 | 1-Dodecene (10 mmol) | DCP (10 mmol) | trimethyl silyl triflate (0.2 mmol) | 41% |
| II-12 | 1-Dodecene (10 mmol) | DCP (10 mmol) | boron trifluoride etherate (0.2 mmol) | 30% |
| II-13 | 1-Dodecene (3 mmol) | DCP (17 mmol) | Triflic Acid (0.2 mmol) | 80% |
| II-14 | 1-Dodecene (3 mmol) | DCP (17 mmol) | trimethyl silyl triflate (0.2 mmol) | 52% |
| II-15 | 1-Dodecene (3 mmol) | DCP (17 mmol) | boron trifluoride etherate (0.2 mmol) | 56% |
| II-16 | Internal dodecenes (17 mmol) | DCP (3 mmol) | Triflic Acid (0.2 mmol) | 82% |
| II-17 | Internal dodecenes (17 mmol) | DCP (3 mmol) | trimethyl silyl triflate (0.2 mmol) | 76% |
| II-18 | Internal dodecenes (17 mmol) | DCP (3 mmol) | boron trifluoride etherate (0.2 mmol) | 12% |
| II-19 | Internal dodecenes (10 mmol) | DCP (10 mmol) | Triflic Acid (0.2 mmol) | 33% |
| II-20 | Internal dodecenes (10 mmol) | DCP (10 mmol) | trimethyl silyl triflate (0.2 mmol) | 22% |
| II-21 | Internal dodecenes (10 mmol) | DCP (10 mmol) | boron trifluoride etherate (0.2 mmol) | 7% |
| II-22 | Internal dodecenes (3 mmol) | DCP (17 mmol) | Triflic Acid (0.2 mmol) | 46% |
| II-23 | Internal dodecenes (3 mmol) | DCP (17 mmol) | trimethyl silyl triflate (0.2 mmol) | 45% |
| II-24 | Internal dodecenes (3 mmol) | DCP (17 mmol) | boron trifluoride etherate (0.2 mmol) | 25% |

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process for preparing an ether compound, the process comprising:
    (a) contacting an olefin and an alcohol with a heterogeneous etherification catalyst in a reaction zone under etherification conditions to form an ether compound;
    (b) removing unconsumed olefin and unreacted alcohol, and the ether compound, to a catalyst free zone;
    (c) repeating steps (a) to (b) using the heterogeneous etherification catalyst and the reaction zone of step (a) and using at least a portion of the unconsumed olefin and unreacted alcohol of step (b) until a desired amount of ether compound accumulates in the catalyst free zone; and
    (d) recovering the ether compound,
wherein the alcohol is selected from the group consisting of: 1,3-dichloro-2-propanol, 2,3-dichloropropanol, 2-chloroethanol, 2-chloro-1,3-propanediol, 3-chloro-1,2-propanediol, and a mixture of two or more thereof and further characterized by the process comprising multiple reactors appropriately connected for transfer of reactants where distillation of the unconsumed olefin and unconsumed alcohol from the ether compound occurs in one vessel that serves as the catalyst free zone during step (c) and liquid olefin and alcohol collected from the distillation is passed into a heated section of pipe or column containing the heterogeneous catalyst that serves as the reaction zone and that is separate from the vessel where distillation occurs before being returned to the catalyst free zone, and further characterized by any solvent in which a process step is run being non-reactive with the olefin, alcohol or catalyst.

2. The process of claim 1 wherein at least one of the olefin or alcohol are located in the catalyst free zone prior to step (a).

3. The process of claim 1 wherein both the olefin and alcohol are located in the catalyst free zone prior to step (a).

4. The process of claim 1 wherein the contacting of step (a) comprises distilling the olefin, the alcohol, or both the olefin and the alcohol from the catalyst free zone into the reaction zone.

5. The process of claim 1 wherein the molar ratio of alcohol to olefin is less than 6:1.

6. The process of claim 1 wherein the reaction zone is at a lower temperature than the catalyst free zone.

7. The process of claim 1 wherein the olefin is a linear or branched alkene or is a cyclic alkene.

8. The process of claim 1 wherein the unconsumed olefin comprises unreacted linear or branched alpha olefin, one or more of its internal isomers, or mixtures thereof.

9. A process for preparing an ether compound, the process consisting of:
    (a) contacting an olefin and an alcohol with a heterogeneous etherification catalyst in a reaction zone under etherification conditions to form an ether compound;
    (b) removing unconsumed olefin and unreacted alcohol, and the ether compound, to a catalyst free zone;

(c) repeating steps (a) to (b) using the heterogeneous etherification catalyst and the reaction zone of step (a) and using at least a portion of the unconsumed olefin and unreacted alcohol of step (b) until a desired amount of ether compound accumulates in the catalyst free zone; and (d) recovering the ether compound, wherein the alcohol is selected from the group consisting of: 1,3-dichloro-2-propanol, 2,3-dichloropropanol, 2-chloroethanol, 2-chloro-1,3-propanediol, 3-chloro-1,2-propanediol, and a mixture of two or more thereof and further characterized by the process comprising multiple reactors appropriately connected for transfer of reactants where distillation of the unconsumed olefin and unconsumed alcohol from the ether compound occurs in one vessel that serves as the catalyst free zone during step (c) and liquid olefin and alcohol collected from the distillation is passed into a heated section of pipe or column containing the heterogeneous catalyst that serves as the reaction zone and that is separate from the vessel where distillation occurs before being returned to the catalyst free zone, and further characterized by any solvent in which a process step is run being non-reactive with the olefin, alcohol or catalyst.

10. The process of claim 1, further characterized by any solvent being present as being selected from a group consisting of toluene, xylene, tetrahydrofuran, diglyme, dioxane, dialkyl ethers, chloroform, and methylene chloride.

11. The process of claim 1, further characterized by the catalyst being selected from a group consisting of triflic acid and trimethylsilyl triflate.

12. The process of claim 9, further characterized by any solvent being present as being selected from a group consisting of toluene, xylene, tetrahydrofuran, diglyme, dioxane, dialkyl ethers, chloroform, and methylene chloride.

13. The process of claim 9, further characterized by the catalyst being selected from a group consisting of triflic acid and trimethylsilyl triflate.

* * * * *